United States Patent
Tsujimori et al.

(10) Patent No.: US 6,995,264 B2
(45) Date of Patent: Feb. 7, 2006

(54) PROCESS FOR PREPARING ARIPIPRAZOLE

(75) Inventors: Hisayuki Tsujimori, Kurume (JP); Tatsuya Yamaguchi, Kurume (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 184 days.

(21) Appl. No.: 10/752,490

(22) Filed: Jan. 8, 2004

(65) Prior Publication Data

US 2004/0192915 A1   Sep. 30, 2004

(30) Foreign Application Priority Data

Jan. 9, 2003   (JP)   ............................. 2003-002996

(51) Int. Cl.
*C07D 401/12*   (2006.01)
(52) U.S. Cl. .................................................... 544/363
(58) Field of Classification Search ................. 544/363
See application file for complete search history.

(56) References Cited

U.S. PATENT DOCUMENTS 4,734,416 A * 3/1988 Banno et al. .......... 514/253.07

FOREIGN PATENT DOCUMENTS

EP   0 367 141 A2   5/1990

OTHER PUBLICATIONS

Oshiro, Y. et al., "Novel Antipsychotic Agents with Dopamine Autoreceptor Agonist Properties: Synthesis and Pharmacology of 7-[4-(4-Phenyl-1-piperazinyl)butoxy]-3,4-dihydro-2(1H)-quinolinone Derivatives", Journal of Medicinal Chemistry, vol. 41, No. 5, pp. 658-667, (1998).
Banno, K. et al., "Studies on 2(1H)-Quinolinone Derivatives as Neuroleptic Agents. I. Synthesis and Biological Activities of (4-Phenyl-1-Piperazinyl)-Propoxy-2(1H)-Quinolinone Derivatives", Chemical and Pharmaceutical Bulletin, Pharmaceutical Society of Japan, Tokyo, Japan, vol. 36, No. 11, pp. 4377-4388, (1988).
Morita, S. et al., "Practical Application of the Palladium-Catalyzed Amination in Phenylpiperazine Synthesis: An Efficient Synthesis of a Metabolite of the Antipsycotic Agent Aripiprazole", Tetrahedron, Elsevier Science Publishers, Amsterdam, Netherlands, vol. 54, No. 19, pp. 4811-4818, (1998).

* cited by examiner

*Primary Examiner*—Emily Bernhardt
(74) *Attorney, Agent, or Firm*—Finnegan, Henderson, Farabow, Garrett & Dunner, L.L.P.

(57)   ABSTRACT

The present invention provides a process for preparing aripiprazole in a high purity and a high yield. According to the process of the present invention, aripiprazole is prepared by the reaction of a carbostyril compound represented by general formula (2):

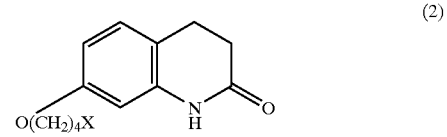

(wherein X is halogen atom, lower alkanesulfonyloxy group, arylsulfonyloxy group or an aralkylsulfonyloxy group), with a piperazine compound represented by formula (3):

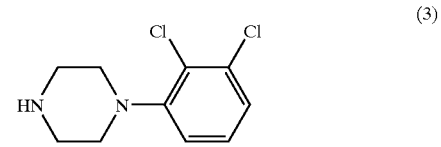

and/or a salt thereof in water, in the presence of 0.5 to 10 mol of an inorganic basic compound, per mol of the carbostyril compound (2).

9 Claims, No Drawings

PROCESS FOR PREPARING ARIPIPRAZOLE

FIELD OF THE INVENTION

The present invention relates to a process for preparing aripiprazole.

BACKGROUND

7-{4-[4-(2,3-Dichlorophenyl)-1-piperazinyl]butoxy}-3,4-dihydro-2(1H)-quinolinone represented by the following formula:

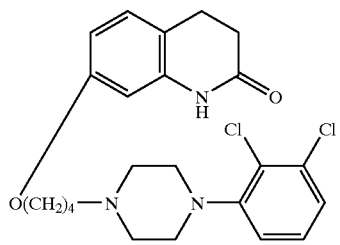

(1)

is called aripiprazole, which is a compound useful as an agent for treating schizophrenia. For instance, a pharmaceutical composition containing aripiprazole is mentioned in EP-A-367141 as an agent for treating schizophrenia, and usefulness of aripiprazole as antipsychotic agents is mentioned in J. Med. Chem., Vol. 41, pp. 658–667 (1998).

Hitherto, aripiprazole has been prepared by a reaction of a carbostyril compound represented by the following general formula (2):

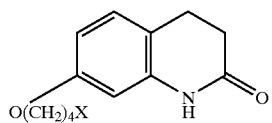

(2)

(wherein X represents a halogen atom, a lower alkanesulfonyloxy group, an arylsulfonyloxy group or an aralkylsulfonyloxy group), with a piperazine compound represented by the following formula (3):

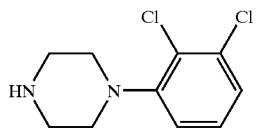

(3)

in the presence of an inorganic or organic basic compound, in an organic solvent or in the absence of solvent. For example, in EP-A-367141, it is mentioned that the above-mentioned reaction can be carried out, if necessary, by adding an alkali metal iodide such as potassium iodide, sodium iodide or the like as the reaction accelerator; and in the working examples thereof (EP-A2-367141, page 5, lines 42–44) sodium iodide is used as the reaction accelerator. According to the process described in EP-A-367141, however, yield of the objective aripiprazole cannot exceed about 80%, even if the reaction accelerator is used.

According to EP-A-367141, the preparation of aripiprazole is carried out even in the absence of solvent. In the absence of solvent, however, the reaction can progress only slowly, and the reaction system is difficult to maintain in a uniform state by stirring, because the starting material compounds and the objective aripiprazole are both solid materials. Accordingly, the process described in EP-A-367141 is not suitable for industrial manufacture.

Further, the process described in EP-A-367141 is complicated in the procedure for obtaining the objective aripiprazole.

Since aripiprazole is used as an active ingredient of pharmaceutical drugs, it is desired to obtain the aripiprazole in a further higher purity. Further, for suppressing the manufacturing cost, it is desired to produce the aripiprazole in a further higher yield.

SUMMARY OF THE INVENTION

It is an object of this invention to provide a process for preparing aripiprazole in higher purity and higher yield.

The present inventors have now discovered a process for preparing aripiprazole in further higher purity and yield. It is a common technical knowledge in the field of chemical science that a chemical reaction can progress in a high efficiency when the substrate of the reaction is dissolved in the reaction system. According to the above-mentioned knowledge, it is virtually impossible for one of ordinary skilled in the art to think of using water as a reaction medium for a reaction between a carbostyril compound of general formula (2), which is entirely insoluble in water, and a piperazine compound of formula (3) or a salt thereof. In addition, the ordinary skilled in the art can easily expect that the group X in the molecule of carbostyril compound represented by general formula (2) has a very high possibility of conversion into a hydroxyl group by hydrolysis with water. Thus, the ordinary skilled in the art can easily expect that purity and yield of aripiprazole will be lowered under such a condition.

Under the conditions mentioned above, the present inventors have remarkably discovered that aripiprazole can be prepared in further higher purity and higher yield by daringly using water, entirely incapable of dissolving the carbostyril compounds of general formula (2), as a reaction medium and further using an inorganic basic compound as said basic compound.

The present invention relates to a process for preparing aripiprazole characterized by reacting a carbostyril compound represented by the above-mentioned general formula (2) with a piperazine compound represented by the formula (3) and/or a salt thereof in water, in the presence of an inorganic basic compound of which amount is in the range of 0.5 to 10 mol per mol of the carbostyril compound (2), in order to obtain aripiprazole represented by the formula (1).

DETAILED DESCRIPTION OF THE INVENTION

The carbostyril compounds represented by the general formula (2) used as a starting material in the present invention are known compounds.

In the general formula (2), the halogen atom represented by X includes a fluorine atom, a chlorine atom, a bromine atom and an iodine atom.

As examples of the lower alkanesulfonyloxy group represented by X, straight or branched chain alkanesulfonyloxy groups having 1–6 carbon atoms such as methanesulfonyloxy group, ethanesulfonyloxy group, isopropanesulfonyloxy group, n-propanesulfonyloxy group, n-butanesulfonyloxy group, tert-butanesulfonyloxy group, n-pentanesulfonyloxy group, n-hexanesulfonyloxy group and the like are encompassed in the present invention.

As the arylsulfonyloxy groups represented by X, for example, phenylsulfonyloxy groups, which may have on the phenyl ring, 1 to 3 groups selected from the group consisting of straight or branched chain alkyl groups having 1–6 carbon atoms, straight or branched chain alkoxy groups having 1–6 carbon atoms, nitro group and halogen atom, as substituents; naphthylsulfonyloxy groups; and the like are encompassed in the present invention. As example of the above-mentioned phenylsulfonyloxy group which may have the above-mentioned substituents, phenylsulfonyloxy group, 4-methylphenylsulfonyloxy group, 2-methylphenylsulfonyloxy group, 4-nitrophenylsulfonyloxy group, 4-methoxyphenylsulfonyloxy group, 2-nitrophenylsulfonyloxy group, 3-nitrophenylsulfonyloxy group, 3-chlorophenylsulfonyloxy group and the like are encompassed in the present invention. As examples of the naphthylsulfonyloxy group, $\alpha$-naphthylsulfonyloxy group, $\beta$-naphthylsulfonyloxy group and the like are encompassed in the present invention.

As the aralkylsulfonyloxy group represented by X, for example, straight or branched chain $C_{1-6}$ alkylsulfonyloxy groups substituted with phenyl group, in which a phenyl ring may have, as substituents, 1 to 3 groups selected from the group consisting of a straight or branched chain alkyl group having 1–6 carbon atoms, a straight or branched chain alkoxy group having 1–6 carbon atoms, a nitro group and a halogen atom; straight or branched chain $C_{1-6}$ alkylsulfonyloxy groups substituted with naphthyl group; and the like are encompassed in the present invention. As examples of the above-mentioned alkylsulfonyloxy group substituted with phenyl group, benzylsulfonyloxy group, 2-phenylethylsulfonyloxy group, 4-phenylbutylsulfonyloxy group, 2-methylbenzylsulfonyloxy group, 4-methoxybenzylsulfonyloxy group, 4-nitrobenzylsulfonyloxy group, 3-chlorobenzylsulfonyloxy group and the like are encompassed in the present invention. As examples of the above-mentioned alkylsulfonyloxy group substituted with naphthyl group, $\alpha$-naphthylmethylsulfonyloxy group, $\beta$-naphthymethylsulfonyloxy group and the like are encompassed in the present invention.

As the X, halogen atoms are preferable, and a chlorine atom is more preferable.

The piperazine compounds represented by the formula (3) and salts thereof which are used in the present invention as another starting material are also known compounds.

As said salt, for example, inorganic salts such as hydrochloride, sulfate, phosphate, hydrobromide and the like; and organic salts such as oxalate, maleate, fumarate, malate, tartrate, citrate, benzoate and the like are encompassed in the present invention.

In the reaction between the above-mentioned carbostyril compound of general formula (2) and the piperazine compound of formula (3) and/or a salt thereof, the ratio between amounts thereof is not particularly limited, and amounts thereof can be selected appropriately from a wide range. The piperazine compound of formula (3) and/or a salt thereof can be more particularly used in an amount of at least 0.5 mol and preferably in an amount of 1 to 1.5 mol, per one mol of the carbostyril compound of general formula (2).

The reaction of the present invention is carried out in water, in the presence of an inorganic basic compound.

As the inorganic basic compound, known ones can be used widely. For example, alkali metal hydroxides such as sodium hydroxide, potassium hydroxide, cesium hydroxide, lithium hydroxide and the like; alkali metal carbonates such as sodium carbonate, potassium carbonate, cesium carbonate, lithium carbonate, lithium hydrogen carbonate, sodium hydrogen carbonate, potassium hydrogen carbonate and the like; alkali metals such as metallic sodium, metallic potassium and the like; etc. are encompassed in the present invention. These inorganic basic compounds are used either in one kind alone or in the form of a mixture of two or more kinds.

In cases of using one kind of inorganic basic compound alone, an alkali metal carbonate such as sodium carbonate, potassium carbonate, cesium carbonate, lithium carbonate, lithium hydrogen carbonate, sodium hydrogen carbonate, potassium hydrogen carbonate or the like is preferable, and the amount thereof is particularly 0.5 to 10 mol and more particularly 0.5 to 6 mol, per one mol of the carbostyril compound represented by the general formula (2).

In cases of using two or more kinds of inorganic basic compounds as a mixture, it is preferable to use an alkali metal hydroxide such as sodium hydroxide, potassium hydroxide, cesium hydroxide, lithium hydroxide or the like in the form of a mixture with an alkali metal carbonate such as sodium carbonate, potassium carbonate, cesium carbonate, lithium carbonate, lithium hydrogen carbonate, sodium hydrogen carbonate, potassium hydrogen carbonate or the like. When such a mixture is used, the total amount of the inorganic basic compounds put to use is particularly 0.5 to 10 mol and more particularly 0.5 to 6 mol, per one mol of the carbostyril compound represented by the general formula (2).

In the process of the present invention, water is used usually in an amount of 3 to 50 parts by weight and preferably in an amount of 5 to 15 parts by weight, per part by weight of the carbostyril compound represented by the general formula (2).

The reaction of the present invention is carried out usually at a temperature ranging from room temperature to 200° C., and preferably from about 80 to 150° C. The reaction is usually completed in about 1 to 10 hours.

The reaction of this invention can be made to progress more advantageously by carrying out the reaction with stirring.

The aripiprazole obtained according to the process of the present invention can be easily isolated from the reaction mixture and purified according to the isolating means and purifying means conventionally employed in this field. As said means for isolation and purification, for example, solvent extraction method, dilution method, recrystallization method, column chromatography, preparative thin layer chromatography and the like can be referred to.

According to the process of this invention, aripiprazole can be prepared in a high purity and a high yield.

Since the reaction of the present invention uses water as the reaction medium, the process of the present invention may avoid the use of substances undesirable from the viewpoint of environmental hygiene such as organic solvents, gives no load to the environment, and is safe.

According to the process of the present invention, aripiprazole can be prepared by a simple procedure.

According to the process of the present invention, aripiprazole with high purity can be prepared without any complicated purifying steps.

Since the process of the present invention uses no reagents exceeding the need, aripiprazole can be prepared economically.

Accordingly, the process of the present invention is quite advantageous as an industrial production process of aripiprazole.

EXAMPLES

Hereunder, the present invention will be further described with reference to working examples.

Example 1

In 600 ml of water was dissolved 36.0 g of potassium carbonate, to which were added 60.0 g of 7-(4-chlorobutoxy)-3,4-dihydrocarbostyril and 69.6 g of 1-(2,3-dichlorophenyl)piperazine monohydrochloride. The mixture was heated with stirring at 90 to 95° C. for about 4 hours. Then, the reaction mixture was cooled to about 40° C., and the deposited crystals were collected by filtration. The crystals thus obtained were washed with 240 ml of water and dissolved in 900 ml of ethyl acetate, and an azeotropic mixture of water/ethyl acetate (about 300 ml) was distilled out under reflux. The remaining solution was cooled to 0 to 5° C., and the deposited crystals were collected by filtration. The crystals thus obtained were washed with 120 ml of ethyl acetate and dried under a reduced pressure of 50 Torr, at 50 to 60° C. for 3 hours to obtain 98.4 g of aripiprazole (yield 92.8%, purity 99%). mp. 140° C.

Purity of the aripiprazole was measured by high performance liquid chromatography (HPLC) under the following conditions:
  Column: YMC AM303 ODS (manufactured by YMC Co.)
  Eluent: 0.02M sodium sulfate/acetonitrile/methanol/acetic acid=56/33/11/1
  Flow rate: 1 ml/min.
  Wave length of detection: 254 nm UV

The invention claimed is:

1. A process for preparing aripiprazole represented by formula (1):

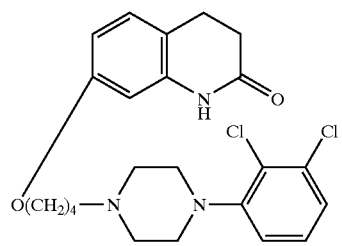

(1)

by reacting a carbostyril compound represented by formula (2):

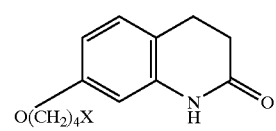

(2)

wherein X represents a halogen atom, a lower alkanesulfonyloxy group, an arylsulfonyloxy group or an aralkylsulfonyloxy group, with a piperazine compound represented by formula (3):

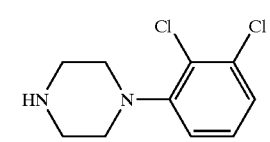

(3)

and/or a salt thereof in water, and in the presence of an inorganic basic compound in an amount from 0.5 to 10 mol per mol of the carbostyril compound (2).

2. A process for preparing aripiprazole according to claim 1, wherein said process uses one kind of inorganic basic compound alone, and said inorganic basic compound is an alkali metal hydroxide, an alkali metal carbonate or an alkali metal.

3. A process for preparing aripiprazole according to claim 1, wherein said process uses two or more kinds of inorganic basic compounds as a mixture, and said mixture of the inorganic basic compounds is a mixture of an alkali metal hydroxide and an alkali metal carbonate.

4. A process for preparing aripiprazole according to claim 2 or 3, wherein X is a halogen atom.

5. A process for preparing aripiprazole according to claim 2, wherein X is a chlorine atom and said inorganic basic compound is an alkali metal carbonate.

6. A process for preparing aripiprazole according to claim 3, wherein X is a chlorine atom.

7. A process for preparing aripiprazole according to claim 2 or 3, wherein said alkali metal hydroxide is sodium hydroxide, potassium hydroxide, cesium hydroxide or lithium hydroxide.

8. A process for preparing aripiprazole according to claim 2, 3 or 5, wherein said alkali metal carbonate is sodium carbonate, potassium carbonate, cesium carbonate, lithium carbonate, lithium hydrogen carbonate, sodium hydrogen carbonate or potassium hydrogen carbonate.

9. A process for preparing aripiprazole according to claim 2, wherein said alkali metal is sodium or potassium.

* * * * *